(12) United States Patent
Clark et al.

(10) Patent No.: US 7,816,574 B2
(45) Date of Patent: Oct. 19, 2010

(54) ALKYLAROMATIC PRODUCTION PROCESS

(75) Inventors: Michael C. Clark, Chantilly, VA (US);
Christine N. Elia, Bridgewater, NJ (US);
Frederick Y. Lo, Middlesex, NJ (US);
Matthew J. Vincent, Baytown, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 471 days.

(21) Appl. No.: 12/019,955

(22) Filed: Jan. 25, 2008

(65) Prior Publication Data

US 2008/0194897 A1     Aug. 14, 2008

Related U.S. Application Data

(60) Provisional application No. 60/900,638, filed on Feb. 9, 2007.

(51) Int. Cl.
*C07C 2/66*     (2006.01)

(52) U.S. Cl. .................................................. 585/467

(58) Field of Classification Search .................. 585/467
See application file for complete search history.

(56) References Cited

U.S. PATENT DOCUMENTS

| | | | |
|---|---|---|---|
| 3,674,680 A | 7/1972 | Hoekstra et al. | |
| 3,751,504 A | 8/1973 | Kcown et al. | |
| 3,751,506 A | 8/1973 | Burress | |
| 3,755,483 A | 8/1973 | Burress | |
| 3,966,644 A | 6/1976 | Gustafson | |
| 4,016,218 A | 4/1977 | Haag et al. | |
| 4,028,227 A | 6/1977 | Gustafson | |
| 4,185,040 A | 1/1980 | Ward et al. | |
| 4,328,130 A | 5/1982 | Kyan | |
| 4,441,990 A | 4/1984 | Huang | |
| 4,547,605 A | 10/1985 | Kresge et al. | |
| 4,891,458 A | 1/1990 | Innes et al. | |
| 4,992,606 A | 2/1991 | Kushnerick et al. | |
| 5,043,509 A | 8/1991 | Imai et al. | |
| 5,118,896 A | 6/1992 | Steigelmann et al. | |
| 5,149,894 A | 9/1992 | Holtermann et al. | |
| 5,258,565 A | 11/1993 | Kresge et al. | |
| 5,334,795 A | 8/1994 | Chu et al. | |
| 5,371,310 A | 12/1994 | Bennett et al. | |
| 5,453,554 A | 9/1995 | Cheng et al. | |
| 5,557,024 A | 9/1996 | Cheng et al. | |
| 6,005,152 A | 12/1999 | Amarilli et al. | |
| 6,077,498 A | 6/2000 | Diaz Cabanas et al. | |
| 6,888,037 B2 | 5/2005 | Dandekar et al. | |
| 2002/0013216 A1 | 1/2002 | Broekhoven et al. | |

FOREIGN PATENT DOCUMENTS

| | | |
|---|---|---|
| CN | 1277893 | 12/2000 |
| CN | 1443603 | 9/2003 |
| DE | 3315105 | 11/1983 |
| EP | 0 432 814 | 6/1991 |
| EP | 0 629 549 | 12/1994 |
| EP | 0 719 750 | 7/1996 |
| EP | 0 732 146 | 9/1996 |
| WO | 97/17290 | 5/1997 |
| WO | 01/21562 | 3/2001 |
| WO | 2004/007072 | 1/2004 |
| WO | 2007/139629 | 12/2007 |

*Primary Examiner*—Thuan Dinh Dang
(74) *Attorney, Agent, or Firm*—Darryl M. Tyus

(57) ABSTRACT

The present disclosure provides a process for selectively producing a desired monoalkylated aromatic compound comprising the step of contacting in a reaction zone an alkylatable aromatic compound with an alkylating agent in the presence of catalyst comprising a porous crystalline material under at least partial liquid phase conditions, said catalyst manufactured from extrudate to comprise catalytic particulate material of from about 125 microns to about 790 microns in size, having an Effectiveness Factor increased from about 25% to about 750% from that of the original extrudate, and having an external surface area to volume ratio of greater than about 79 $cm^{-1}$.

7 Claims, No Drawings

ALKYLAROMATIC PRODUCTION PROCESS

PRIORITY CLAIM

This application claims the benefit of U.S. Provisional Application No. 60/900,638, filed Feb. 9, 2007, the entirety of which is incorporated by reference.

BACKGROUND OF THE INVENTION

The present disclosure relates to a process mechanism for producing alkylaromatics, especially monoalkylaromatic compounds, for example ethylbenzene, cumene and sec-butylbenzene.

The alkylaromatic compounds ethylbenzene and cumene, for example, are valuable commodity chemicals which are used industrially for the production of styrene monomer and coproduction of phenol and acetone respectively. In fact, a common route for the production of phenol comprises a process which involves alkylation of benzene with propylene to produce cumene, followed by oxidation of the cumene to the corresponding hydroperoxide, and then cleavage of the hydroperoxide to produce equal molar amounts of phenol and acetone. Ethylbenzene may be produced by a number of different chemical processes. One process which has achieved a significant degree of commercial success is the vapor phase alkylation of benzene with ethylene in the presence of a solid, acidic ZSM-5 zeolite catalyst. Examples of such ethylbenzene production processes are described in U.S. Pat. No. 3,751,504 (Keown), U.S. Pat. No. 4,547,605 (Kresge) and U.S. Pat. No. 4,016,218 (Haag).

Another process which has achieved significant commercial success is the liquid phase process for producing ethylbenzene from benzene and ethylene since it operates at a lower temperature than the vapor phase counterpart and hence tends to result in lower yields of by-products. For example, U.S. Pat. No. 4,891,458 (Innes) describes the liquid phase synthesis of ethylbenzene with zeolite Beta, whereas U.S. Pat. No. 5,334,795 (Chu) describes the use of MCM-22 in the liquid phase synthesis of ethylbenzene.

Cumene has for many years been produced commercially by the liquid phase alkylation of benzene with propylene over a Friedel-Crafts catalyst, particularly solid phosphoric acid or aluminum chloride. More recently, however, zeolite-based catalyst systems have been found to be more active and selective for propylation of benzene to cumene. For example, U.S. Pat. No. 4,992,606 (Kushnerick) describes the use of MCM-22 in the liquid phase alkylation of benzene with propylene.

Typically, the zeolite catalysts employed in hydrocarbon conversion processes, such as aromatics alkylation, are in the form of cylindrical extrudates. However, it is known from, for example, U.S. Pat. No. 3,966,644 (Gustafson) that shaped catalyst particles having a high surface to volume ratio, such as those having a polylobal cross-section, can produce improved results in processes which are diffusion limited, such as the hydrogenation of reside.

Moreover, it is known from U.S. Pat. No. 4,441,990 (Huang) that a polylobal catalyst particle having a non-cylindrical centrally located aperture can reduce the diffusion path for reagents and the pressure drop across packed catalyst beds while minimizing catalyst loss due to breakage, abrasion and crushing. In particular, Example 8 of the '990 patent discloses that hollow trilobal and quadrulobal ZSM-5 catalysts are more active and selective for the ethylation of benzene at 410° C. and 2169 kPa-a (kilopascal absolute) pressure than solid cylindrical catalysts of the same length. Under these conditions, the reagents are necessarily in the vapor phase.

Current commercial catalysts used most often for these process mechanisms are 0.159 cm cylindrical or 0.127 cm quadrulobal extrudates. The prior extrudates are roughly 1550 to 1600 microns in size, and the latter are roughly 1250 to 1300 microns in size.

Existing alkylation processes for producing alkylaromatic compounds, for example ethylbenzene and cumene, inherently produce polyalkylated species as well as the desired monoalkylated product. It is therefore normal to transalkylate the polyalkylated species with additional aromatic feed, for example benzene, to produce additional monoalkylated product, for example ethylbenzene or cumene, either by recycling the polyalkylated species to the alkylation reactor or, more frequently, by feeding the polyalkylated species to a separate transalkylation reactor. Examples of catalysts which have been used in the alkylation of aromatic species, such as alkylation of benzene with ethylene or propylene, and in the transalkylation of polyalkylated species, such as polyethylbenzenes and polyisopropylbenzenes, are listed in U.S. Pat. No. 5,557,024 (Cheng) and include MCM-49, MCM-22, PSH-3, SSZ-25, zeolite X, zeolite Y, zeolite Beta, acid dealuminized mordenite and TEA-mordenite. Transalkylation over a small crystal (<0.5 micron) form of TEA-mordenite is also disclosed in U.S. Pat. No. 6,984,764 (Roth et al).

Where the alkylation step is performed in the liquid phase, it is also desirable to conduct the transalkylation step under liquid phase conditions. However, by operating at relatively low temperatures, liquid phase processes impose increased requirements on the catalyst, particularly in the transalkylation step where the bulky polyalkylated species must be converted to additional monoalkylated product without producing unwanted by-products. This has proven to be a significant problem in the case of cumene production where existing catalysts have either lacked the desired activity or have resulted in the production of significant quantities of by-products such as ethylbenzene and n-propylbenzene.

U.S. Pat. No. 6,888,037 (Dandekar et al) discloses a process for producing cumene which comprises the step of contacting benzene and propylene under at least partial liquid phase alkylating conditions with a particulate molecular sieve alkylation catalyst, wherein the particles of said alkylation catalyst have a surface area to volume ratio of about 80 to less than 200 inch$^{-1}$. According to U.S. Pat. No. 6,888,037, the liquid phase propylation of benzene, unlike the liquid phase ethylation of benzene, is sensitive to intraparticle (macroporous) diffusion limitations. In particular, by selecting the shape and size of the particles of the alkylation catalyst such that the surface to volume ratio is within the specified range, the intraparticle diffusion distance can be decreased without excessively increasing the pressure drop across the first catalyst bed. As a result, the activity of the catalyst for the propylation of benzene can be increased, while at the same time the selectivity of the catalyst towards undesirable polyalkylated species, such as diisopropylbenzene (DIPB) can be reduced.

U.S. Patent Application Ser. No. 60/808,192 discloses a process for producing a monoalkylated aromatic compound in an alkylation reaction zone, said process comprising the steps of (1) providing said alkylation reaction zone with an alkylatable aromatic compound, an alkylating agent, and a catalytic particulate material; and (2) contacting said alkylatable aromatic compound and said alkylating agent with said catalytic particulate material in said alkylation reaction zone maintained under alkylation conditions, to form a product comprised of said monoalkylated aromatic compound and polyalkylated aromatic compound(s), wherein the majority of said catalytic particulate material has a surface area to volume ratio of greater than about 79 cm$^{-1}$.

According to the present disclosure, it has now unexpectedly been found that the reaction of the present disclosure conducted in the presence of a specific catalyst manufactured from extrudate to comprise catalytic particulate material within the narrow range of from about 125 microns to about 790 microns in size and having an Effectiveness Factor, hereafter defined, increased from about 25% to about 750% from that of the original extrudate, yields a unique combination of activity and selectivity while not subjecting the process to unacceptable pressure drop across the catalyst bed. This is especially the case when the process involves liquid phase alkylation for manufacture of monoalkylated product, particularly for the liquid phase alkylation of benzene to ethylbenzene or cumene. This obviates the demand in many instances for the difficult transalkylation reaction for conversion of unwanted bulky polyalkylated species in such a process.

SUMMARY OF THE INVENTION

According to the present disclosure, there is provided an improved process for selectively producing a desired monoalkylated aromatic compound comprising the step of contacting in a reaction zone an alkylatable aromatic compound with an alkylating agent in the presence of catalyst comprising a porous crystalline material under at least partial liquid phase conditions, the catalyst manufactured from extrudate to comprise catalytic particulate material of from about 125 microns to about 790 microns in size and having an Effectiveness Factor, hereafter defined, increased from about 25% to about 750% from that of the original extrudate. An aspect of the present disclosure is an improved alkylation process for the selective production of monoalkyl benzene in a reaction zone comprising the step of reacting benzene with an alkylating agent under alkylation conditions sufficient to cause alkylation in the presence of alkylation catalyst comprising a porous crystalline material, the catalyst manufactured from extrudate to comprise catalytic particulate material of from about 125 microns to about 790 microns in size and having an Effectiveness Factor, hereafter defined, increased from about 25% to about 750% from that of the original extrudate. The catalyst for use in the present process may comprise, for example, a MCM-22 family material, a crystalline molecular sieve having the structure of zeolite Beta, or one having an X-ray diffraction pattern including d-spacing maxima at 12.4±0.25, 6.9±0.15, 3.57±0.07 and 3.42±0.07 Angstroms, the catalyst manufactured from extrudate to comprise catalytic particulate material of from about 125 microns to about 790 microns in size and having an Effectiveness Factor, hereafter defined, increased from about 25% to about 750% from that of the original extrudate. More particularly, the catalyst for use herein may comprise a crystalline molecular sieve having the structure of Beta, a MCM-22 family material, e.g. MCM-22, or a mixture thereof.

The catalyst for use in the present disclosure preferably comprises a MCM-22 family material, such as for example a crystalline silicate having the structure of MCM-22, PSH-3, SSZ-25, ERB-1, ITQ-1, ITQ-2, ITQ-30, MCM-36, MCM-49, MCM-56 and mixtures thereof.

DETAILED DESCRIPTION OF THE INVENTION

All patents, patent applications, test procedures, priority documents, articles, publications, manuals, and other documents cited herein are fully incorporated by reference to the extent such disclosure is not inconsistent with the present disclosure and for all jurisdictions in which such incorporation is permitted.

When numerical lower limits and numerical upper limits are listed herein, ranges from any lower limit to any upper limit are contemplated.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "MCM-22 family material" (or "material of the MCM-22 family" or "molecular sieve of the MCM-22 family"), as used herein, includes:

molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;

molecular sieves made from a common second degree building block, a 2-dimensional tiling of such MWW framework type unit cells, forming a "monolayer of one unit cell thickness", preferably one c-unit cell thickness;

molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, and any combination thereof, or molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), MCM-56 (described in U.S. Pat. No. 5,362,697), and UZM-8 (described in U.S. Pat. No. 6,756,030). The entire contents of the patents are incorporated herein by reference.

It is to be appreciated the MCM-22 family molecular sieves described above are distinguished from conventional large pore zeolite alkylation catalysts, such as mordenite, in that the MCM-22 family materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

The present disclosure relates to an improved process mechanism for production of monoalkylated aromatic compounds, particularly ethylbenzene, cumene or sec-butylbenzene, by the liquid or partial liquid phase alkylation of an alkylatable aromatic compound, particularly benzene. More particularly, the present process uses a catalyst composition comprising a porous crystalline material, the catalyst manufactured from extrudate to comprise catalytic particulate material of from about 125 microns to about 790 microns in size and having an Effectiveness Factor, hereafter defined, increased from about 25% to about 750% from that of the original extrudate, more specifically from about 260 microns to about 700 microns in size with an Effectiveness Factor, hereafter defined, increased from about 50% to about 650% from that of the original extrudate. The catalyst composition for use in the present disclosure will comprise catalytic particulate material having an external surface area to volume ratio of greater than about 79 $cm^{-1}$, more specifically from greater than about 79 $cm^{-1}$ to about 374 $cm^{-1}$.

Effectiveness Factor is commonly defined as the rate of reaction in the presence of mass transport limitations divided by the rate of reaction without mass transport limitation. A detailed discussion of Effectiveness Factor can be found in general treatises on this subject, such as "Mass Transfer in Heterogeneous Catalysis" by C. N. Satterfield; and "Mass Transfer in Heterogeneous Catalysis", Robert Krieger Publishing Co., Malabar, Fla., 1980, original edition, M.I.T. Press, Cambridge, Mass., 1970, incorporated herein by reference. In some circumstances when the catalyst deactivates during the measurement, the reaction rate constant is measured excluding the effect of catalyst deactivation, such as the reaction rate constant measured by extrapolating the reaction rate prior to deactivation. In the present disclosure, effectiveness factor is calculated as the rate constant of the alkylation reaction of the catalyst being tested divided by the rate constant of the alkylation reaction without mass transfer limitation. The calculation of the rate constant of the alkylation reaction is based upon a solution for the second order rate expression in a batch reactor which can also be found in "Elements of Chemical Reaction Engineering", Fogler, H. Scott, P T R Prentice-Hall, Inc., 1992, §8.3.1 & §5.6.2. Further details for batch cumene testing can be found in the subsequent section "Test Sequence for Cumene Manufacture in a Batch Test." The second order rate constant measured at conditions without mass transfer limitation is calculated by estimating from the measured rates what the maximum rate of reaction would be with an infinitely small particle, wherein the rate constant is measured at conditions without deactivation, such as by extrapolating the reaction rate prior to deactivation The term "aromatic" in reference to the alkylatable aromatic compounds which may be useful as feedstock herein is to be understood in accordance with its art-recognized scope. This includes alkyl substituted and unsubstituted mono- and polynuclear compounds. Compounds of an aromatic character that possess a heteroatom may also be useful provided sufficient catalytic activity is maintained under the reaction conditions selected.

Substituted aromatic compounds that can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups that do not interfere with the alkylation reaction.

Suitable aromatic compounds include benzene, naphthalene, anthracene, naphthacene, perylene, coronene, and phenanthrene, with benzene being preferred.

Generally the alkyl groups that can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, n-propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic compounds can also be used as starting materials and include aromatic organics such as are produced by the alkylation of aromatic organics with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as n-propyl benzene and xylenes respectively. These by-products made in such instances may be less than about 100 wppm.

Reformate containing a mixture of benzene, toluene and/or xylene constitutes a particularly useful feed for the alkylation process of this disclosure.

The alkylating agents that may be useful in the process of this disclosure generally include any aliphatic or aromatic organic compound having one or more available alkylating aliphatic groups capable of reaction with the alkylatable aromatic compound, preferably with the alkylating group possessing from 1 to 5 carbon atoms. Examples of suitable alkylating agents are olefins such as ethylene, propylene, the butenes such as, for example, 1-butene, 2-butene or isobutylene, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth. Mixtures of these compounds may also be useful, such as, for example, propylene and propanol mixtures.

Mixtures of light olefins are useful as alkylating agents in the alkylation process of this disclosure. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents. For example, a typical FCC light olefin stream possesses the following composition:

|  | Wt. % | Mole % |
|---|---|---|
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Reaction products that may be obtained from the process of the present disclosure include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes. Particularly preferred process mechanisms of the disclosure relate to the production of cumene by the alkylation of benzene with propylene and production of ethylbenzene by the alkylation of benzene with ethylene.

The reactants can be partially or completely in the liquid phase and can be neat, i.e. free from intentional admixture or dilution with other material, or they can be brought into contact with the catalyst composition with the aid of carrier gases or diluents such as, for example, hydrogen, methane and/or nitrogen.

The alkylation process of this disclosure may be conducted such that the organic reactants, i.e., the alkylatable aromatic compound and the alkylating agent, are brought into contact with the presently required catalyst in a suitable reaction zone under effective alkylation conditions. Such conditions include a temperature of from about 0° C. to about 500° C., preferably from about 10° C. to about 260° C., a pressure of from about 20 to about 25000 kPa-a, preferably from about 100 to about 5500 kPa-a, a molar ratio of alkylatable aromatic compound to alkylating agent of from about 0.1:1 to about 50:1, preferably from about 0.5:1 to about 10:1, and a feed weight hourly space velocity (WHSV) based on the alkylating agent of from about 0.1 to 500 $hr^{-1}$, preferably from about 0.1 to about 100 $hr^{-1}$.

When benzene is alkylated with ethylene to produce ethylbenzene, the alkylation reaction is preferably carried out in the liquid phase under conditions including a temperature of from about 150° C. to about 300° C., more preferably from about 170° C. to about 260° C.; a pressure up to about 20400 kPa-a, more preferably from about 2000 kPa-a to about 5500 kPa-a; a weight hourly space velocity (WHSV) based on the ethylene alkylating agent of from about 0.1 to about 20 $hr^{-1}$, more preferably from about 0.5 to about 6 $hr^{-1}$; and a ratio of benzene to ethylene in the alkylation reaction zone of from about 0.5:1 to about 100:1 molar, preferably 0.5:1 to 50:1 molar, more preferably from about 1:1 to about 30:1 molar, most preferably from about 1:1 to about 10:1 molar.

When benzene is alkylated with propylene to produce cumene, the reaction may also take place under liquid phase conditions including a temperature of up to about 250° C., preferably up to about 150° C., e.g., from about 10° C. to about 125° C.; a pressure of about 25000 kPa-a or less, e.g., from about 100 to about 3000 kPa-a; a weight hourly space velocity (WHSV) based on propylene alkylating agent of from about 0.1 $hr^{-1}$ to about 250 $hr^{-1}$, preferably from about 1 $hr^{-1}$ to about 50 $hr^{-1}$; and a ratio of benzene to propylene in the alkylation reaction zone of from about 0.5:1 to about 100:1 molar, preferably 0.5:1 to 50:1 molar, more preferably from about 1:1 to about 30:1 molar, most preferably from about 1:1 to about 10:1 molar.

When benzene is alkylated with a butene to produce sec-butylbenzene, the reaction may also take place under liquid phase conditions including a temperature of up to about 250° C., preferably up to about 150° C., e.g., from about 10° C. to about 125° C.; a pressure of about 25000 kPa-a or less, e.g., from about 1 to about 3000 kPa-a; a weight hourly space velocity (WHSV) based on the butene alkylating agent of from about 0.1 $hr^{-1}$ to about 250 $hr^{-1}$, preferably from about 1 $hr^{-1}$ to about 50 $hr^{-1}$; and a ratio of benzene to butene in the alkylation reaction zone of from about 0.5:1 to about 100:1 molar, preferably 0.5:1 to 50:1 molar, more preferably from about 1:1 to about 30:1 molar, most preferably from about 1:1 to about 10:1 molar.

The reaction zone useful for the present disclosure due to the small particulate size of the catalyst may be, for example, in a fixed bed operation with low linear velocity so as not to create unacceptable pressure drop; in a continuous stirred tank reactor (CSTR); in an ebullating bed operating in up-flow mode such that the catalyst moves in an ebullating fashion; or in a slurry loop in which the catalyst and feedstock form a loose slurry pumped through a pipe serving as the reactor.

A fixed bed operation useful in the present disclosure with low linear velocity so as not to create unacceptable pressure drop is depicted in "Elements of Chemical Reaction Engineering", Fogler, H. Scott, P T R Prentice-Hall, Inc., 1992, §4.4 & §8.3.2, and "Perry's Chemical Engineers' Handbook", 7th ed., Perry, Robert H. and Green, Don W., McGraw-Hill Companies, Inc., 1997, §23, incorporated herein by reference.

A continuous stirred tank reactor (CSTR) useful in the present disclosure is depicted in "Elements of Chemical Reaction Engineering", Fogler, H. Scott, P T R Prentice-Hall, Inc., 1992, §8.3.1 & §5.6.2, and "Perry's Chemical Engineers' Handbook", 7th ed., Perry, Robert H. and Green, Don W., McGraw-Hill Companies, Inc., 1997, §23, incorporated herein by reference.

An ebullating bed useful in the present disclosure operating in up-flow mode such that the catalyst moves in an ebullating fashion is depicted in "Perry's Chemical Engineers' Handbook", 7th ed., Perry, Robert H. and Green, Don W., McGraw-Hill Companies, Inc., 1997, §23, incorporated herein by reference.

A slurry reactor in which the catalyst and feedstock form loose slurry stirred in a tank or pumped through a pipe serving as the reactor useful in the present disclosure is depicted in "Chemical and Catalytic Reaction Engineering: Carberry, James J., McGraw-Hill, Inc., 1976, §10.6 and "Perry's Chemical Engineers' Handbook", 7th ed., Perry, Robert H. and Green, Don W., McGraw-Hill Companies, Inc., 1997, §23, incorporated herein by reference.

The catalyst for use in the present disclosure may comprise a crystalline molecular sieve having the structure of zeolite Beta (described in U.S. Pat. No. 3,308,069) or an MWW structure type such as, for example, those having an X-ray diffraction pattern including d-spacing maxima at 12.4±0.25, 6.9±0.15, 3.57±0.07 and 3.42±0.07 Angstroms. Examples of MWW structure type materials include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in U.S. Pat. No. 6,231,751), ITQ-30 (described in WO 2005-118476), MCM-36 (described in U.S. Pat. No. 5,250,277), MCM-49 (described in U.S. Pat. No. 5,236,575) and MCM-56 (described in U.S. Pat. No. 5,362,697). The catalyst can include the molecular sieve in unbound or self-bound form or, alternatively, the molecular sieve can be combined in a conventional manner with an oxide binder as hereinafter detailed. For the improvement of the present disclosure, the average particle size of the catalyst manufactured from extrudate must be from about 125 microns to about 790 microns in size and have an Effectiveness Factor increased from about 25% to about 750% from that of the original extrudate. More specifically, the catalyst manufactured from extrudate will be from about 260 microns to about 700 microns in size with an Effectiveness Factor increased by from about 50% to about 650%. Also, the external surface area to volume ratio of the catalyst will be greater than about 79 cm$^{-1}$, preferably from greater than about 79 cm$^{-1}$ to about 374 cm$^{-1}$.

For the reaction process of the present disclosure, the alkylation reactor effluent contains excess aromatic feed, monoalkylated product, polyalkylated products, and various impurities. The aromatic feed is recovered by distillation and recycled to the alkylation reactor. Usually a small bleed is taken from the recycle stream to eliminate unreactive impurities from the loop. The bottoms from the distillation may be further distilled to separate monoalkylated product from polyalkylated products and other heavies.

Any polyalkylated products separated from the alkylation reactor effluent may be reacted with additional aromatic feed in a transalkylation reactor, separate from the alkylation reactor, over a suitable transalkylation catalyst. The transalkylation catalyst may comprise one or a mixture of crystalline molecular sieves having the structure of zeolite Beta, zeolite Y, mordenite or a MCM-22 family material having an X-ray diffraction pattern including d-spacing maxima at 12.4±0.25, 6.9±0.15, 3.57±0.07 and 3.42±0.07 Angstroms.

The X-ray diffraction data used to characterize the above catalyst structures are obtained by standard techniques using the K-alpha doublet of copper as the incident radiation and a diffractometer equipped with a scintillation counter and associated computer as the collection system. Materials having the above X-ray diffraction lines include, for example, MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in U.S. Pat. No. 6,231,751), ITQ-30 (described in WO 2005-118476), MCM-36 (described in U.S. Pat. No. 5,250,277), MCM-49 (described in U.S. Pat. No. 5,236,575) and MCM-56 (described in U.S. Pat. No. 5,362,697), with MCM-22 being particularly preferred.

Zeolite Beta is disclosed in U.S. Pat. No. 3,308,069. Zeolite Y and mordenite occur naturally but may also be used in one of their synthetic forms, such as Ultrastable Y (USY), which is disclosed in U.S. Pat. No. 3,449,070, Rare earth exchanged Y (REY), which is disclosed in U.S. Pat. No. 4,415,438, and TEA-mordenite (i.e., synthetic mordenite prepared from a reaction mixture comprising a tetraethylammonium directing agent, "R"), which is disclosed in U.S. Pat. Nos. 3,766,093 and 3,894,104. However, in the case of TEA-mordenite for use in the transalkylation catalyst, the particular synthesis regimes described in the patents noted lead to the production of a mordenite product composed of predominantly large crystals with a size greater than 1 micron and typically around 5 to 10 micron. It has been found that controlling the synthesis so that the resultant TEA-mordenite has an average crystal size of less than 0.5 micron results in a transalkylation catalyst with materially enhanced activity for liquid phase aromatics transalkylation.

The small crystal TEA-mordenite desired for transalkylation can be produced by crystallization from a synthesis mixture having a molar composition within the following ranges:

| | Useful | Preferred |
|---|---|---|
| R/R+Na+ = | >0.4 | 0.45-0.7 |
| OH-/SiO2 = | <0.22 | 0.05-0.2 |
| Si/Al2 = | >30-90 | 35-50 |
| H$_2$O/OH = | 50-70 | 50-60 |

The crystallization from this synthesis mixture is conducted at a temperature of 90 to 200° C., for a time of 6 to 180 hours.

The catalyst for use in the present disclosure may include an inorganic oxide material matrix or binder. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

Specific useful catalyst matrix or binder materials employed herein include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of crystalline molecular sieve and binder or matrix, if present, may vary widely with the crystalline molecular sieve content ranging from about 1 to about 99 percent by weight, and more usually in the range of about 30 to about 80 percent by weight of the total catalyst. Of course, the catalyst may comprise a self-bound molecular sieve or an unbound molecular sieve, thereby being about 100% crystalline molecular sieve.

The catalyst for use in the present disclosure, or its crystalline molecular sieve component, may or may not contain added functionalization, such as, for example, a metal of Group 6 (e.g. Cr and Mo), Group 7 (e.g. Mn and Re) or Groups 8, 9, and 10 (e.g. Co, Ni, Pd and Pt), or phosphorus.

The catalyst for use in the present disclosure must be manufactured form extrudate and have an average particle size within the narrow range of from about 125 to about 790 microns and have an Effectiveness Factor increased from about 25% to about 750% from that of the original extrudate, for example, from about 260 to about 700 microns in size with an Effectiveness Factor increased from about 50% to about 650% from that of the original extrudate. It may be made, for example, by reducing the particle size of 0.159 cm cylindrical extrudates or 0.127 cm shaped, e.g. trilobal or quadrulobal, extrudates by crushing and sieving. A summary of the molecular sieves and/or zeolites, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known techniques, like spray drying, prilling, pelletizing and extrusion, have been and are being used to produce macrostructures in the form of, for example, spherical particles, extrudates, pellets and tablets of both microporous and other types of porous materials for use in catalysis, adsorption and ion exchange. A summary of these techniques is described in "Catalyst Manufacture," A. B. Stiles and T. A. Koch, Marcel Dekker, New York, 1995.

Non-limiting examples of the present disclosure involving an alkylation mechanism are described with reference to the following experiments. In the experiments, catalyst activity is defined by reference to the kinetic rate constant which is determined by assuming second order reaction kinetics. For a discussion of the determination of the kinetic rate constant, reference is directed to "Heterogeneous Reactions: Analysis, Examples, and Reactor Design, Vol. 2: Fluid-Fluid-Solid Reactions" by L. K. Doraiswamy and M. M. Sharma, John Wiley & Sons, New York (1994) and to "Chemical Reaction Engineering" by O. Levenspiel, Wiley Eastern Limited, New Delhi (1972).

Catalysts for Testing

In these experiments, catalyst materials tested are listed below:

"Material 1" was MCM-49 catalyst that was prepared by extruding a mixture of 80 wt. % MCM-49 crystals and 20 wt. % alumina into solid quadrulobal extrudates having a diameter of 0.127 cm and a length of 0.635 cm (hereinafter "MCM-49 quadrulobal catalyst"). The resultant catalyst particles had a surface area to volume ratio of 78 $cm^{-1}$ and an Effectiveness Factor of 0.18.

"Material 2" was prepared from Material 1 by crushing and sieving the 0.127 cm MCM-49 quadrulobal catalyst to a range of particle sizes from 250 to 297 microns. The resultant catalyst particles had a surface area to volume ratio of 344 $cm^{-1}$ and an Effectiveness Factor of 0.65. The increase in Effectiveness Factor from the Material 1 catalyst was 261%.

"Material 3" was MCM-22 catalyst that was prepared by extruding a mixture of 65 wt. % MCM-22 crystals and 35 wt. % alumina into solid cylindrical extrudates having a diameter of 0.159 cm and a length of 0.635 cm (hereinafter "MCM-22 cylindrical catalyst"). The resultant MCM-22 cylindrical catalyst particles had a surface area to volume ratio of 34.6 $cm^{-1}$ and an Effectiveness Factor of 0.08.

"Material 4" was prepared from Material 3 by crushing and sieving the 0.159 cm MCM-22 cylindrical catalyst to a range of particle sizes from 250 to 297 microns. The resultant catalyst particles had a surface area to volume ratio of 344 $cm^{-1}$ and an Effectiveness Factor of 0.55. The increase in Effectiveness Factor from the Material 3 catalyst was 587%.

"Material 5" was zeolite Beta catalyst that was prepared by extruding a mixture of 80 wt. % zeolite Beta crystals and 20 wt. % alumina into solid quadrulobal extrudates having a diameter of 0.127 cm (1/20 inch) and a length of 0.635 cm (hereinafter "Beta quadrulobal catalyst"). The resultant Beta quadrulobal catalyst particles had a surface area to volume ratio of 78 $cm^{-1}$ and an Effectiveness Factor of 0.21 based on the second order rate constant measured by extrapolating the reaction rate prior to deactivation and without mass transport limitations.

"Material 6" was prepared from Material 5 by crushing and sieving the 0.127 cm Beta quadrulobal catalyst to a range of particle sizes from 250 to 297 microns. The resultant catalyst particles had a surface area to volume ratio of 344 $cm^{-1}$ and an Effectiveness Factor of 0.73 based on the second order rate constant measured by extrapolating the reaction rate prior to deactivation and without mass transport limitations. The increase in Effectiveness Factor from the Material 5 catalyst is 347%.

Catalyst Reactivity Measurement Procedure

Equipment for Batch Tests

A 300 ml Parr batch reaction vessel for cumene manufacture and a 600 ml Parr batch reaction vessel for ethylbenzene manufacture were each equipped with a stir rod and static catalyst basket was used for the activity and selectivity measurements. The reaction vessels were fitted with two removable vessels for the introduction of benzene and propylene or ethylbenzene respectively.

Feed Pretreatment

Benzene

Benzene was obtained from a commercial source. The benzene was passed through a pretreatment vessel (2L Hoke vessel) containing equal parts (by volume) molecular sieve 13x, molecular sieve 4A, Engelhard F-24 Clay, and Selexsorb CD (in order from inlet to outlet), and then through a 250 ml vessel containing MCM-22 catalyst. All feed pretreatment materials were dried in a 260° C. oven for 12 hours before using.

Propylene and Ethylene

Propylene and ethylene were obtained from a commercial specialty gases source and were polymer grade. The propylene and ethylene were passed through a 300 ml vessel containing pretreatment materials in the following order:
  a. 150 ml molecular sieve 5A
  b. 150 ml Selexsorb CD Both guard-bed materials were dried in a 260° C. oven for 12 hours before using.

Nitrogen

Nitrogen was ultra high purity grade and obtained from a commercial specialty gases source. The nitrogen was passed through a 300 ml vessel containing pretreatment materials in the following order:
  a. 150 ml molecular sieve 5A
  b. 150 ml Selexsorb CD Both guard-bed materials were dried in a 260° C. oven for 12 hours before using.

Catalyst Preparation and Loading

A 2 gram sample of catalyst was dried in an oven in air at 260° C. for 2 hours. The catalyst was removed from the oven and immediately 1 gram of catalyst was weighed. Quartz chips were used to line the bottom of a basket followed by loading of the catalyst into the basket on top of the first layer of quartz. Quartz chips were then placed on top of the catalyst. The basket containing the catalyst and quartz chips was placed in an oven at 260° C. overnight in air for about 16 hours.

The reactor and all lines were cleaned with a suitable solvent (such as toluene) before each experiment. The reactor and all lines were dried in air after cleaning to remove all traces of cleaning solvent. The basket containing the catalyst and quartz chips was removed from the oven and immediately placed in the reactor and the reactor was immediately assembled.

Test Sequence for Cumene Manufacture in a Batch Test

The reactor temperature was set to 170° C. and purged with 100 sccm of the ultra high purity nitrogen for 2 hours. After nitrogen purged the reactor for 2 hours, the reactor temperature was reduced to 130° C., the nitrogen purge was discontinued and the reactor vent closed. A 156.1 gram quantity of benzene was loaded into a 300 ml transfer vessel, performed in a closed system. The benzene vessel was pressurized to 790 kPa-a with the ultra high purity nitrogen and the benzene was transferred into the reactor. The agitator speed was set to 500 rpm and the reactor was allowed to equilibrate for 1 hour.

A 75 ml Hoke transfer vessel was then filled with 28.1 grams of liquid propylene and connected to the reactor vessel, and then connected with 2169 kPa-a ultra high purity nitrogen. After the one-hour benzene stir time had elapsed, the propylene was transferred from the Hoke vessel to the reactor. The 2169 kPa-a nitrogen source was maintained connected to the propylene vessel and open to the reactor during the entire run to maintain constant reaction pressure during the test. Liquid product samples were taken at 30, 60, 120, 150, 180 and 240 minutes after addition of the propylene.

Test Sequence for Ethylbenzene Manufacture in a Batch Test

The reactor temperature was set to 170° C. and purged with 100 sccm of the ultra high purity nitrogen for 2 hours. After nitrogen purged the reactor for 2 hours, the reactor temperature was reduced to 220° C., the nitrogen purge was discontinued and the reactor vent closed. A 195 gram quantity of benzene was loaded into a 600 ml transfer vessel, performed in a closed system. The benzene vessel was pressurized to 790 kPa-a with the ultra high purity nitrogen and the benzene was transferred into the reactor. The agitator speed was set to 500 rpm and the reactor was allowed to equilibrate for 1 hour. After the one-hour benzene stir time had elapsed, 39.4 grams of ethylene was introduced into the reactor. A 2169 kPa-a nitrogen source was maintained connected to the reaction vessel during the entire run to maintain constant reaction pressure during the test. Liquid product samples were taken at 30, 60, 120, 150, 180 and 240 minutes after addition of the ethylene.

Test Sequence for Cumene Manufacture in a Fixed Bed Test

These experiments were conducted in a fixed bed ⅜" or ¾" OD tubular reactor in a downflow configuration. The reactor furnace was controlled in isothermal mode. The catalyst was dried off-line at 260° C. in air for 2 hours before loading into the reactor. Experiments were conducted with catalyst as whole extrudates loaded into the ⅜" reactor. The catalyst bed was axially centered in the middle furnace zone. The catalyst used was extrudate form, spray-dried form, or extrudate crushed and sized to 250 microns to 297 microns depending on the experiment. All catalysts were packed with inert sand to fill the interstitial void spaces. Reaction conditions were 125° C., 2169 kPa-a and the benzene/propylene molar ratio was 2.8/1. Weight hourly space velocity was adjusted during the experiments and ranged from 1 $hr^{-1}$ to 320 $hr^{-1}$ on a propylene basis.

At reactor start-up, the reactor was brought to reaction pressure of 2169 kPa-a with the ultra high purity nitrogen, and heated to reaction temperature of 125° C. prior to introducing the feed. The catalyst was allowed to equilibrate for 1 to 2 days to achieve steady state before data was collected.

The MCM-49 quadrulobal catalyst (Material 1), the MCM-22 cylindrical catalyst (Material 3), and the 250 to 297 micron catalysts (average of 274 microns) prepared from them by crushing and sieving (Materials 2 and 4, respectively) were tested according the cumene batch test procedure. The MCM-49 quadrulobal catalyst (Material 1) and the 250 to 297 micron catalyst (average of 274 microns) prepared from it by crushing and sieving (Material 2) were tested according the ethylbenzene batch test procedure. The MCM-49 quadrulobal catalyst (Material 1), the Beta cylindrical catalyst (Material 5), and the 250 to 297 micron catalysts (average of 274 microns) prepared from them by crushing and sieving (Materials 2 and 6, respectively) were tested according the cumene fixed bed procedure.

Example 1

In these experiments, cumene was manufactured by contacting 5.55 parts by weight benzene and 1 part by weight propylene in the batch slurry reactor using the procedure detailed above for Test Sequence for Cumene Manufacture in a Batch Test over catalysts selected individually from Materials 1, 2 and 3. Cumene (isopropylbenzene, IPB) and diisopropylbenzene (DIPB) products were collected from each experiment and it was found that catalyst for use in the present disclosure, i.e. Material 2, provided about 30% reduction in the DIPB/IPB ratio. Also, Material 2 yielded about 288% higher activity than Material 1, and about 600% higher activity than Material 3.

Example 2

In these experiments, cumene was manufactured by contacting 5.55 parts by weight benzene and 1 part by weight propylene in the batch slurry reactor using the procedure detailed above for Test Sequence for Cumene Manufacture in a Batch Test over catalyst comprising the 0.127 cm MCM-49 quadrulobal catalyst (Material 1) and the 250 to 297 micron catalyst prepared from it by crushing and sieving (Material 2). Cumene (isopropylbenzene, IPB) and diisopropylbenzene (DIPB) products were collected from each experiment and it was found that Material 2 again provided a 30% reduction in the DIPB/IPB ratio.

Example 3

In these experiments, cumene was manufactured by contacting 5.55 parts by weight benzene and 1 part by weight propylene in the batch slurry reactor using the procedure detailed above for Test Sequence for Cumene Manufacture in a Batch Test over catalyst comprising the MCM-22 cylindrical catalyst (Material 3) and the 250 to 297 micron catalyst prepared from it by crushing and sieving (Material 4). Cumene (isopropylbenzene, IPB) and diisopropylbenzene (DIPB) products were collected from each experiment and it was found that catalyst Material 4 provided a 13% reduction in the DIPB/IPB ratio.

Example 4

In these experiments, ethylbenzene was manufactured by contacting 0.95 parts by weight benzene and 1 part by weight ethylene in the batch slurry reactor using the procedure detailed above for Test Sequence for Ethylbenzene Manufacture in a Batch Test over catalyst comprising the 0.127 cm MCM-49 quadrulobal catalyst (Material 1) and the 250 to 297 micron catalyst prepared from it by crushing and sieving (Material 2). Ethylbenzene (EB) and diethylbenzene (DEB) products were collected from each experiment and it was found that catalyst Material 2 provided a 23% reduction in the DEB/EB ratio.

Example 5

In these experiments, cumene was manufactured by contacting 5.2 parts by weight benzene and 1 part by weight propylene in the fixed bed micro reactor using the procedure detailed above for Test Sequence for Cumene Manufacture in a Fixed Bed Test over catalyst comprising the 0.127 cm MCM-49 quadrulobal catalyst (Material 1) and the 250 to 297 micron catalyst prepared from it by crushing and sieving (Material 2). Cumene (isopropylbenzene, IPB) and diisopropylbenzene (DIPB) products were collected from each experiment and it was found that Example 8 provided a 54% reduction in the DIPB/IPB ratio.

Example 6

In these experiments, cumene was manufactured by contacting 5.2 parts by weight benzene and 1 part by weight propylene in the batch slurry reactor using the procedure detailed above for Test Sequence for Cumene Manufacture in a Batch Test over catalyst comprising the Beta quadrulobal catalyst (Material 5) and the 250 to 297 micron catalyst prepared from it by crushing and sieving (Material 6). Cumene (isopropylbenzene, IPB) and diisopropylbenzene (DIPB) products were collected from each experiment and it was found that catalyst Material 6 provided a 65% reduction in the DIPB/IPB ratio before deactivation.

Example 7

In a simulated CSTR reaction conducted in the liquid phase at 130° C., 2413 kPa-a inlet pressure and WHSV of 76.5 hr$^{-1}$ based on propylene, the catalyst volume of 16.8 m$^3$ comprising catalyst Material 1, feedstock comprising 25 parts by weight propylene and 75 parts by weight benzene, propylene conversion was 32.4%. By simulating the same CSTR reaction with catalyst comprising the MCM-49 quadrulobal catalyst having been crushed and sieved to be 250 to 297 microns in size (Material 2), propylene conversion was found to be 66.2%. This example shows that in a continuous stirred tank reactor, catalyst particles sized to be within the requirements of the present disclosure are effective in increasing conversion of propylene in reaction with benzene in the liquid phase.

All patents, patent applications, test procedures, articles, publications, and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated.

While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

What is claimed is:

1. In a process for manufacturing a monoalkylated aromatic compound in a reaction zone, said process comprising contacting a feedstock comprising an alkylatable aromatic compound and an alkylating agent with a catalytic particulate material at alkylation reaction conditions, the improvement wherein said catalytic particulate material is manufactured from extrudate and comprises particles of from about 125 microns to about 790 microns in size having an Effectiveness Factor increased from about 25% to about 750% from that of the original extrudate, and has an external surface area to volume ratio of greater than about 79 cm$^{-1}$, wherein the catalytic particulate material comprises porous crystalline material selected from the group consisting of a MCM-22, MCM-49, zeolite Beta and mixtures thereof, wherein said alkylating agent is ethylene, said alkylatable aromatic compound is benzene and said monoalkylated aromatic compound is ethylbenzene, or wherein said alkylating agent is propylene, said alkylatable aromatic compound is benzene and said monoalkylated aromatic compound is cumene.

2. The process of claim 1 wherein said catalytic particulate material comprises particles of from about 260 microns to about 700 microns in size having an Effectiveness Factor increased from about 50% to about 650% from that of the original extrudate and has an external surface area to volume ratio of from greater than about 79 cm$^{-1}$ to about 374 cm$^{-1}$.

3. The process of claim 1 wherein said reaction conditions include a temperature of from about 0° C. to about 500° C., a pressure of from about 0.2 to about 25000 kPa-a, a molar ratio of alkylatable aromatic compound to alkylating agent of from about 0.1:1 to about 50:1, and a feed weight hourly space velocity (WHSV) based on the alkylating agent of from about 0.1 to 500 hr$^{-1}$.

4. The process of claim 1 wherein said reaction zone is in at least one of a fixed bed reactor, a continuous stirred tank reactor, and an ebullating bed reactor operating in up-flow mode.

5. The process of claim 1 wherein said reaction zone is in a slurry loop reactor in which the catalytic particulate material and feedstock form loose slurry pumped through a pipe.

6. The process of claim 1 wherein said reaction conditions include a temperature of from about 150° C. to about 300° C., a pressure up to about 20400 kPa-a, a weight hourly space velocity (WHSV) based on the ethylene alkylating agent of from about 0.1 to about 20 hr$^{-1}$, and a ratio of benzene to ethylene in the reaction zone of from about 0.5:1 to about 50:1 molar.

7. The process of claim 1 wherein said reaction conditions include a temperature of up to about 250° C., a pressure of about 25000 kPa-a or less, a weight hourly space velocity (WHSV) based on propylene alkylating agent of from about 0.1 hr$^{-1}$ to about 250 hr$^{-1}$, and a ratio of benzene to propylene in the reaction zone of from about 0.5:1 to about 50:1 molar.

* * * * *